United States Patent [19]
Kitai et al.

[11] Patent Number: 4,900,843
[45] Date of Patent: Feb. 13, 1990

[54] METHOD FOR DIMERIZATION OF AROMATIC HALIDE COMPOUNDS

[75] Inventors: Mitsumasa Kitai; Yoshio Katsuro; Shigenori Kawamura; Masumi Hino, all of Kitakyushu; Keiichi Sato, Tokyo, all of Japan

[73] Assignee: Mitsubishi Chemical Industries Limited, Japan

[21] Appl. No.: 200,615

[22] Filed: May 31, 1988

[30] Foreign Application Priority Data

Dec. 2, 1987 [JP] Japan .................................. 62-304981

[51] Int. Cl.$^4$ ............................................. C07D 307/89
[52] U.S. Cl. .................................... 549/252; 562/481; 562/488
[58] Field of Search ................. 562/481, 488; 549/252

[56] References Cited

U.S. PATENT DOCUMENTS 4,720,576  1/1988  Wada et al. ......................... 562/488

Primary Examiner—Richard L. Raymond
Attorney, Agent, or Firm—Jordan B. Bierman

[57] ABSTRACT

A method of dehalogeno-dimerizing an aromatic halide compound substituted by at least one halogen atom substituted on the aromatic ring using a palladium catalyst on support in the presence of water, a reducing agent and a halogen acceptor is disclosed. The method is characterized by using the palladium catalyst on support immersed in a hydrohalogenic acid prior to the dehalogeno-dimerization reaction.

25 Claims, No Drawings

METHOD FOR DIMERIZATION OF AROMATIC HALIDE COMPOUNDS

FIELD OF THE INVENTION

The present invention relates to a process for producing dimers of aromatic compounds in high yield by dehalogeno-dimerization of aromatic halide compounds.

BACKGROUND OF THE INVENTION

Dimers of aromatic compounds are useful as starting materials for various industrial products. For example, alkali metal salts of 3,4,3', 4'-biphenyltetracarboxylic acids are very useful as starting materials for the production of heat-resistant polyimide resins.

A method is known to produce biphenyl compounds from aromatic halide compounds by dehalogeno-dimerizing them in the presence of a palladium catalyst, water and methanol (see Japanese Patent Examined Publication No. 14015/84). Various improvements of this method have been proposed, which comprise replacing methanol by polyhydric alcohols or formaldehyde [see Japanese Patent Publication (OPI) No. 26238/87 (the term "OPI" as used herein means an "unexamined published Japanese patent application")], formic acid or formates [see Synthesis Communications, 538 (1978), as well as Japanese Patent Publication (OPI) Nos. 137838/86 and 167642/86], and carbon monoxide [see Japanese Patent Publication (OPI) No. 293932/86]. However, even these modifications are insufficient to attain the desired biphenyl compounds in satisfactorily high yields and further improvements in this respect have been desired.

The present inventors conducted intensive studies in order to develop a process for producing biaryl compounds in high yield by dehalogeno-dimerization of aromatic halide compounds. As a result, the present inventors found that in the known method of dehalogeno-dimerizing aromatic halide compounds using palladium catalysts on supports, biaryl compounds could be produced in high yield when the palladium catalysts on supports had been immersed in hydrohalogenic acids such as hydrochloric acid prior to the dehalogenodimerization reaction.

SUMMARY OF THE INVENTION

The gist of the present invention lies in a method for dehalogeno-dimerizing an aromatic halide compound having at least one halogen atom substituted on the aromatic ring using a palladium catalyst on support in the presence of water, a reducing agent and a halogen acceptor, which comprises using the palladium catalyst on support immersed in a hydrohalogenic acid prior to the dehalogeno-dimerization reaction.

DETAILED DESCRIPTION OF THE PREFERRED EMBODIMENT

The starting material used in the present invention is an aromatic halide compound having at least one halogen atom substituted on the aromatic ring. The aromatic halide compound is usually monocyclic. An example of halogen atom, at least one of which is substituted on the aromatic ring, is iodine, bromine or chlorine, with bromine and chlorine being preferred. It is particularly advantageous to use chlorine because chlorine is inexpensive. If two or more halogen atoms are substituted on the aromatic ring, the halogens may be the same or different. The halogen atoms on the aromatic ring are usually one or two, with substitution by one halogen atom being particularly preferred. The aromatic ring of the aromatic halide compound may have one or more substituents other than at least one halogen atom, with the number of such substituents being preferably one or two. If a carbon atom adjacent to the carbon atom substituted by the halogen atom has another substituent or if a plurality of halogen atoms are adjacent to each other, it will sometimes occur that the yield of the biaryl compound is reduced.

Specific examples of the aromatic halide compound that can be used in the method of the present invention include chlorobenzene, p-chlorobromobenzene, p-chlorobiphenyl, p-chlorophenol, p-chloroanisole, p-chlorobenzamide, p-chloroaniline, p-chloronitrobenzene, p-chlorobenzophenone, p-chloroacetophenone, sodium p-chlorobenzenesulfonate, p-chlorobenzoic acid and salts thereof with alkali metals such as lithium, sodium and potassium, p-chlorobenzonitrile, m-bromobenzoic acid and salts thereof with alkali metals such as lithium, sodium and potassium, β-chloronaphthalene, 4-chloroorthoxylene, 4-chlorophthalic acid and salts thereof with alkali metals such as lithium, sodium and potassium, 4-chlorophthalic anhydride, and 4,5-dichlorophthalic acid. These aromatic halide compounds may be used either alone or in combination.

In carrying out the present invention, it is advantageous to use aromatic halide compounds soluble in aqueous alkaline solution, it therefore being desirable to use monocyclic aromatic halide compounds substituted by 1 or 2 carboxyl or hydroxyl groups. Specifically, monohalogenophthalic acid, alkali metal salts of monohalogenophthalic acid, and monohalogenophthalic acid anhydride are preferred. It is particularly advantageous to use 4-chlorophthalic acid, salts thereof with alkali metals or acid anhydrides thereof either independently or as admixtures containing one of these compounds as the chief component because alkali metals of 3,4,3', 4'-biphenyltetracarboxylic acids serving as starting materials for heat-resistant polyimides can be obtained.

Water is either used as a solvent for the aromatic halide compound if the compound is soluble in aqueous alkaline solution or directly added to the reaction system. Water generally is used in an amount of at least 0.1 vol %, preferably at least vol %, of the reaction mixture containing the aromatic halide compound, palladium catalyst, reducing agent and halogen acceptor. If the aromatic halide compound is soluble in aqueous alkaline solution, water is advantageously used in a solvent quantity. If the aromatic halide compound is not soluble in aqueous alkaline solution, the use of a large quantity of water sometimes may rather reduce the yield of the biaryl compound, so the quantity of water is preferably used within a range of 1 to 60 vol %. If the quantity of water is less than 1 vol % or if no water is added at all, the yield and selectivity of the biaryl compound will undesirably decrease.

Examples of the reducing agent used in dehalogeno-dimerization reaction in the present invention include alcohols, carbon monoxide, chloroform, formaldehydes and so on. Illustrative alcohols include monohydric alcohols such as methanol, ethanol and propanol; dihydric alcohols such as ethylene glycol, propylene glycol, 1,2-butanediol, 1,3-propanediol and 1,4-butanediol; trihydric alcohols such as glycerin; and tetrahydric alcohols such as pentaerythritol. Illustrative formaldehydes include paraformaldehyde and formalin.

If the reducing agent is selected from alcohols, chloroform and formaldehydes, it generally is used in an amount of 0.01 to 50 moles, preferably 0.1 to 10 moles, per mole of the aromatic halide compound used as a starting material. If carbon monoxide is used as a reducing agent, its partial pressure is adjusted to lie between 0.1 and 60 kg/cm$^2$, preferably between 1 and 10 kg/cm$^2$. The carbon monoxide used may be pure or may be mixed with nitrogen or other gases.

Among the reducing agents above, alcohols and carbon monoxide are preferred, with alcohols being particularly preferred. Polyhydric alcohols are more preferred and the intended reaction of the present invention is advantageously carried out when glycerin or ethylene glycol is used as the reducing agent.

In the process of the present invention, the presence of a halogen acceptor in the reaction system is essential for obtaining the biaryl compound in high yield. Any substance that is capable of accepting halogen atoms that are produced during dehalogeno-dimerization reactions may be used as a halogen acceptor, with basic substances being generally used. Illustrative basic substances that can be used as halogen acceptors include ammonia, alkali metal compounds, and alkaline earth metal compounds. Among these, alkali metal compounds and alkaline earth metal compounds are advantageous; they are exemplified by hydroxides of alkali metals or alkaline earth metals, salts thereof with inorganic acids such as carbonic acid, nitric acid, phosphoric acid and boric acid, salts of alkali metals or alkaline earth metals with organic acids such as acetic acid and phthalic acid, and alkoxides of alkali metals or alkaline earth metals.

Preferred examples include alkali metal or alkaline earth metal hydroxides such as lithium hydroxide, sodium hydroxide, potassium hydroxide, magnesium hydroxide, calcium hydroxide and barium hydroxide; alkali metal or alkaline earth metal carbonates such as sodium carbonate, potassium carbonate and sodium hydrogencarbonate; and alkali metal or alkaline earth metal alkoxides such as sodium methoxide, sodium ethoxide and potassium tertiary butoxide. Hydroxides of alkali metals or alkaline earth metals are particularly preferred.

The amount of these halogen acceptors to be used is not limited to any particular value since it varies with the number of halogen atoms and the presence or absence of acidic substituents such as a carboxyl group in the aromatic halide compound used as a starting material. These halogen acceptors generally are used in amounts ranging from 0.01 to 100 moles, preferably 0.1 to 20 moles, per mole of the aromatic halide compound. If the amount of the halogen acceptor used is outside the specified range, undesired results will occur such as the decrease in the yield of the biaryl compound.

The palladium catalyst on support suitable for use in the present invention is prepared by supporting metallic palladium on an appropriate carrier such as activated carbon, silica, alumina, silica-alumina, titanium oxide, magnesia, diatomaceous earth, graphite, barium carbonate, calcium carbonate or zeolite. A particularly advantageous catalyst is palladium-on-activated carbon. Metallic palladium is usually supported in an amount of 0.1 to 20 wt %, preferably 0.5 to 10 wt %, of the carrier.

The palladium catalyst on support generally is used in an amount of 100 to 0.001 milligram atom, preferably 30 to 0.1 milligram atom, of palladium per mole of the aromatic halide compound. In the present invention, it is permitted for the palladium catalyst to contain a catalytic promoter such as ruthenium, gold, nickel or cerium in an amount of no more than 20 wt % of palladium.

It is essential of the present invention that the palladium catalyst on support be subjected to immerse in a hydrohalogenic acid prior to dehalogeno-dimerization reaction. Examples of the hydrohalogenic acid are hydrochloric acid, hydrobromic acid and hydroiodic acid, with hydrochloric acid being particularly preferred. The concentration of the hydrohalogenic acid in which the palladium catalyst is to be immersed generally ranges from 10 to 0.001 wt %, preferably from 1 to 0.01 wt %. If the concentration of the hydrohalogenic acid is too low, the activity of the palladium catalyst will not be fully improved. The temperature for immersion in the hydrohalogenic acid generally ranges from 5° to 70° C., preferably from 10° to 40° C. The immersion time which varies with the concentration of hydrohalogenic acid, the temperature for immersion or other factors generally ranges from about 5 minutes to about 3 hours, preferably from 10 minutes to 1.5 hours. The palladium catalyst on support that has been immersed in the hydrohalogenic acid is filtered either immediately or after neutralizing the hydrohalogenic acid with an alkali, and provided to dehalogenodimerization reaction as the catalyst. If desired, the suspension of the palladium catalyst on support that has been immersed in the hydrohalogenic acid may be directly supplied into the reactor for dehalogeno-dimerization reaction, with reaction being subsequently commenced by addition of an alkali.

Examples of the alkali that may be used to neutralize the hydrohalogenic acid solution after immersion include alkali metal compounds, alkaline earth metal compounds, ammonia, amines and pyridines. The pH of the solution after neutralization is preferably in the range of 5 to 12.

The palladium catalyst on support which is to be subjected to the immersion may be a freshly prepared catalyst or one which is recovered after being used in dehalogeno-dimerization reaction. In either case, the catalyst activity is improved over the catalyst that is not subjected to the immersion. From the viewpoint of catalytic activity, it is more preferable to wash the recovered catalyst with a water-miscible aliphatic organic solvent such as methanol, propanol, acetic acid, propionic acid, tetrahydrofuran or dimethylformamide prior to immersion in a hydrohalogenic acid. The washing may generally be conducted by the same method as employed to perform the immersion treatment.

In accordance with the present invention, the aromatic halide compound is subjected to dehalogeno-dimerization reaction in the presence or absence of a solvent using the palladium catalyst on support that has been immersed in a hydrohalogenic acid. Solvents need not be particularly used if the starting aromatic halide compound is soluble in aqueous alkaline solution. If solvents are used, they must be inert to the reactions. Suitable solvents may be selected from ether compounds such as tetrahydrofuran and dioxane, ketone compounds such as acetone, diethyl ketone and methyl ethyl ketone, and ester compounds such as ethylene glycol diacetate. The amount of these solvents used is not limited to any particular value but may generally be selected from the range of 0.01 to 100 parts per part of the aromatic halide compound.

In order to perform the method of the present invention, a mixture of the aromatic halide compound, the palladium catalyst on support that has been immersed in a hydrohalogenic acid, water, a reducing agent and a halogen acceptor is heated generally at 20° to 250° C., preferably at 50° to 200° C., in the absence or presence of a solvent. The reaction pressure generally ranges from atmospheric pressure to 200 kg/cm$^2$, preferably from atmospheric pressure to 100 kg/cm$^2$. If desired, the reaction may be carried out in the presence of an inert gas. The reaction time is not limited to any particular value and may be properly selected depending upon such factors as a type of the starting material, an amount of catalyst used, a reaction temperature and pressure. Usually, a reaction time ranges from about 10 minutes to about 24 hours.

The method of the present invention may be performed by batch, semi-continuous or continuous system.

In accordance with the present invention, the yield of the desired biaryl compound can be improved by using the palladium catalyst on support immersed in a hydrohalogenic acid. If desired, the reaction mixture successively may be subjected to additional reduction by adding at least one post-reducing agent selected from hydrogen, formic acid, salts thereof and hydrazines after the time when the dehalogeno-dimerization reaction have been substantially completed. If this reduction is done, the yield of the desired biaryl compound is further improved. The additional reduction is particularly effective when the starting material of the dehalogeno-dimerization reaction is either a monohalogenophthalic acid, a salt thereof with an alkali metal or a monohalogenophthalic acid anhydride, with best results being attained if the starting material is either 4-chlorophthalic acid, a salt thereof with an alkali metal, or 4-chlorophthalic acid anhydride. The "time when the dehalogenodimerization reaction have been substantially completed" means the time when the conversion of the aromatic halide compound has reached at least 90%, preferably at least 95%.

The post-reducing agent is used in the additional reduction treatment in an amount that generally ranges from 0.01 to 10 moles, preferably from 0.05 to 1 mole, per mole of the aromatic halide compound. If hydrogen is used as the post-reducing agent, its partial pressure is adjusted to lie between about 0.5 and about 50 kg/cm$^2$. Formic acid salts suitable for use as post-reducing agents are sodium formate and potassium formate. Hydrazines suitable for use as post-reducing agents include hydrazine, phenylhydrazine and methylhydrazine.

The temperature for the additional reduction lies between 50° and 200° C., preferably between 80° and 150° C. The reduction time may range from 10 minutes to 5 hours, preferably from 0.5 to 3 hours. If desired, the additional reduction may be performed with a suitable post-reducing catalyst such as a platinum group metal being added to the reaction mixture.

The biaryl compound obtained by the dehalogeno-dimerization reaction in the practice of the present invention is separated from the reaction mixture by a suitable method such as evaporation, distillation, crystallization, precipitation with an acid or by some other method that is properly selected in accordance with the physical properties of that compound.

In accordance with the method of the present invention, a biaryl compound is produced from an aromatic halide compound in high yield by performing dehalogeno-dimerization reaction in the presence of a palladium catalyst on support that is immersed in a hydrohalogenic acid prior to the dehalogeno-dimerization. Therefore, the method of the present invention is very useful in industrial applications.

The catalyst recovered after the dehalogeno-dimerization reaction can be reactivated by immersing it in a hydrohalogenic acid. The desired biaryl compound can be obtained in high yield by repeatedly using such a regenerated catalyst.

The present invention is hereinafter described in detail with reference to examples. It should, however, be noted that the present invention is by no means limited to the following examples and that various modifications can be made without departing from the scope and the spirit of the invention. Unless otherwise indicated, all parts, percents and ratios are by weight.

EXAMPLE 1

Immersion of Pd Catalyst in HCl

A Pyrex beaker (volume, 100 ml) was charged with 2.35% palladium on carbon containing 52.99% water (product of Japan Engelhardt Co., Ltd.) in an amount of 1.90 g (44.65 mg, 0.420 mmol as Pd) and 35 ml of 0.365% HCl. The mixture was stirred for 30 minutes with a magnetic stirrer and thereafter adjusted to a pH of 11 with 25% aqueous sodium hydroxide. Following 10-minute stirring, the mixture was filtered through filter paper No. 5C (product of Toyo Roshi Kaisha, Ltd.) to obtain a HCl immersed palladium catalyst on carbon.

Dehalogeno-dimerization Reaction

A stainless steel separable flask having volume of 500 ml was charged with all of the HCl immersed Pd on carbon obtained above, 58.89 g of a white powder mainly comprised of monosodium 4-chlorophthalate (containing 145.4 mmol of monosodium 4-chlorophthalate, 20.0 mmol of monosodium 3-chlorophthalate, 9.3 mmol of monosodium 4,5-dichlorophthalate, 8.0 mmol of monosodium 3,4-dichlorophthalate, and 77.8 mmol of monosodium phthalate), 27.76 g (659.3 mmol) of 95 wt % sodium hydroxide, 137.4 ml of demineralized water and 14.1 g (153.1 mmol) of glycerin. After equipping the flask with a reflux condenser and a stirrer, the mixture was heated with stirring for 5 hours at atmospheric pressure and 107° C.

After the reaction, the reaction mixture was analyzed by liquid chromatography and a desired sodium salt of 3,4,3',4'-biphenyltetracarboxylic acid (hereinafter abbreviated as S-BTC salt) was found to have been produced. The results are shown in Table 1.

EXAMPLE 2

Catalyst immersion and dehalogeno-dimerization reactions were performed as in Example 1 except that the palladium catalyst was immersed in 0.037% HCl. The results are shown in Table 1.

COMPARATIVE EXAMPLE 1

The procedures of Example 1 were repeated except that no catalyst immersion was conducted. The results are shown in Table 1.

TABLE 1

| | Catalyst Immersion | | | |
|---|---|---|---|---|
| Example No. | Reducing agent | HCl Concentration (%) | Time (min) | Conversion* (mol %) | Yield of** S—BTC salt (mol %) |
| 1 | glycerin | 0.365 | 30 | 99.8 | 64 |
| 2 | glycerin | 0.037 | 30 | 99.6 | 59 |
| Comparative Example 1 | glycerin | — | — | 99.6 | 53 |

*Conversion (mol %) =

$$\frac{\text{Charged 4-chlorophthalic acid salt (mmol)} - \text{Residual 4-chlorophthalic acid salt (mmol)}}{\text{Charged 4-chlorophthalic acid salt (mmol)}} \times 100$$

**Yield of S—BTC salt (mol %) =

$$\frac{\text{Product S—BTC salt (mmol)} \times 2}{\text{Charged 4-chlorophthalic acid salt (mmol)}} \times 100$$

EXAMPLE 3

Catalyst immersion and dehalogeno-dimerization reaction were performed as in Example 1 except that the palladium catalyst was immersed in 0.809% hydrobromic acid. The results are shown in Table 2.

EXAMPLE 4

Catalyst immersion and dehalogeno-dimerization reaction were performed as in Example 1 except that the palladium catalyst was immersed in 0.510% hydrobromic acid. The results are shown in Table 2.

TABLE 2

| | Catalyst Immersion | | | |
|---|---|---|---|---|
| Example No. | Reducing agent | HBr Concentration (%) | Time (min) | Conversion (mol %) | Yield of S-BTC salt (mol %) |
| 3 | glycerin | 0.809 | 30 | 96.1 | 56.3 |
| 4 | glycerin | 0.510 | 30 | 99.5 | 58.9 |

EXAMPLE 5

The procedures of Example 1 were repeated except that glycerin used as a reducing agent was replaced by 9.83 g (307.2 mmol) of methanol. The results are shown in Table 3.

COMPARATIVE EXAMPLE 2

The procedure of Example 5 were repeated except that no catalyst immersion was effected. The results are shown in Table 3.

TABLE 3

| | Catalyst Immersion | | | |
|---|---|---|---|---|
| Example No. | Reducing agent | HCl Concentration (%) | Time (min) | Conversion (mol %) | Yield of S-BTC salt (mol %) |
| 5 | methanol | 0.365 | 30 | 100 | 48 |
| Comparative Example 2 | methanol | — | — | 99.5 | 44 |

EXAMPLE 6

Immersion of Pd Catalyst in HCl

A Pyrex beaker (volume, 1,000 ml) was charged with 5% palladium on carbon containing 51.2 wt % water (product of Japan Engelhardt Co., Ltd.) in an amount of 18.7 g (456 mg, 4.29 mmol as Pd) and 400 ml of 0.365 wt % HCl. The mixture was stirred for 30 minutes with a magnetic stirrer and thereafter adjusted to a pH of 11 with 25% aqueous sodium hydroxide. Following 10-minute stirring, the mixture was filtered through filter paper No. 5C (Toyo Roshi Kaisha, Ltd.) to obtain a HCl immersed palladium catalyst on carbon and dried at 80° C. for 15 hours.

Dehalogeno-dimerization Reaction

A Pyrex conical flask having a volume of 200 ml was charged with 32 g of crude monosodium 4-chlorophthalate, then with 100 ml of demineralized water and 7 g of sodium hydroxide. The mixture was stirred with a magnetic stirrer to make a solution. Into the solution, 0.4 g of activated carbon was charged and the mixture was stirred for an additional 3 hours. Thereafter, the mixture was filtered through a membrane filter (Toyo Roshi Kaisha, Ltd.), thereby obtaining an aqueous solution of the activated carbon treated crude sodium 4-chlorophthalate. During the filtration, 20 ml of demineralized water was used for washing under shaking. The aqueous solution of the crude sodium 4-chlorophthalate contained 76.60 mmol of sodium 4-chlorophthalate, 16.17 mmol of sodium 3-chlorophthalate, 5.18 mmol of sodium 4,5-dichlorophthalate, 4.06 mmol of sodium 3,4-dichlorophthalate, and 30.21 mmol of sodium phthalate.

A stainless steel autoclave of SUS-316 (volume, 300 ml) equipped with an induction stirrer was charged with all of the aqueous solution of the activated carbon treated crude sodium 4-chlorophthalate. Subsequently, the autoclave was charged with the HCl-immersed 5% palladium on carbon in an amount of 1.2 g (0.56 mmol as Pd), 28.5 g of sodium hydroxide and 30 ml of demineralized water. The mixture was heated up to 120° C. with stirring in a carbon monoxide atmosphere and thereafter the pressure in the system was raised to 1.5 kg/cm$^2$·G with carbon monoxide. The intended reactions were carried out for 3.5 hours with a constant pressure by replenishing carbon monoxide. Thereafter, the reaction temperature was lowered and the palladium on carbon was separated by filtration. The resulting reaction solution was analyzed by liquid chromatography to determine the yield of S-BTC salt. The results are shown in Table 4.

COMPARATIVE EXAMPLE 3

The procedures of Example 6 were repeated except that no catalyst immersion was conducted. The results are shown in Table 4.

TABLE 4

| Example No. | Reducing agent | Catalyst Immersion HCl Concentration (%) | Time (min) | Conversion (mol %) | Yield of S-BTC salt (mol %) |
|---|---|---|---|---|---|
| 6 | CO | 0.365 | 30 | 100 | 79.0 |
| Comparative Example 3 | CO | — | — | 99 | 76.7 |

EXAMPLE 7

Immersion of Pd Catalyst in HCl

A Pyrex beaker (volume, 500 ml) was charged with 2.39 wt % palladium on carbon containing 52.16% water (product of Japan Engelhardt Co., Ltd.) in an amount of 10.92 g (261.2 mg, 2.455 mmol as Pd) and 200 ml of 0.365% HCl. The mixture was stirred for 30 minutes with a magnetic stirrer and thereafter adjusted to a pH of 11 with 25% aqueous sodium hydroxide. Additional stirring was conducted for 10 minutes.

Dimerization

A stainless steel autoclave (1.5 l) equipped with an induction stirrer was charged with all of the slurry of HCl immersed palladium on carbon obtained above, 353.3 g of a white powder mainly comprised of monosodium 4-chlorophthalate (containing 872.3 mmol of monosodium 4-chlorophthalate, 172.6 mmol of monosodium 3-chlorophthalate, 53.5 mmol of monosodium 4,5-dichlorophthalate, 37.5 mmol of monosodium 3,4-dichlorophthalate, and 405.3 mmol of monosodium phthalate), 632.9 g (3955.5 mmol) of 25% aqueous sodium hydroxide, 176.3 ml of demineralized water and 84.8 g (920.7 mmol) of glycerin. The mixture was heated with stirring for 3 hours at 120° C. in a nitrogen atmosphere. Upon analysis by liquid chromatography, it was found that a desired S-BTC salt had been produced in 60.5 mol % yield in the reaction mixture. The conversion of the starting material was 99.9 mol %.

Additional Reduction

Subsequently, the reaction mixture was stirred for 3 hours at 9.5 kg/cm$^2$G and 150° C. in a hydrogen atmosphere. Upon analysis by liquid chromatography, it was found that the yield of S-BTC salt in the reaction mixture increased to 64.5 mol %.

EXAMPLE 8

A stainless steel autoclave (volume, 1.5 l) equipped with an induction stirrer was charged with 2.35 wt % palladium on carbon containing 52.99% water (product of Japan Engelhardt Co., Ltd.) in an amount of 5.55 g (130.5 mg, 1.23 mmol as Pd), 176.7 g of a white powder mainly comprised of monosodium 4-chlorophthalate (containing 436.1 mmol of monosodium 4-chlorophthalate, 86.3 mmol of monosodium 3-chlorophthalate, 26.8 mmol of monosodium 4,5-dichlorophthalate, 18.7 mmol of monosodium 3,4-dichlorophthalate, and 202.6 mmol of monosodium phthalate), 83.3 g of 95% sodium hydroxide (1978.4 mmol), 421.2 ml of demineralized water, and 42.4 g (460.0 mmol) of glycerin. The mixture was heated with stirring for 3 hours at 120° C. under a nitrogen stream. Thereafter, the reaction mixture was stirred for 2 hours at 9.5 kg/cm$^2$G and 140° C. under a hydrogen atmosphere.

After the reaction, the palladium on carbon was filtered out through filter paper No. 5C (Toyo Roshi Kaisha, Ltd.) and the resulting reaction product was analyzed by liquid chromatography to determine the yield of S-BTC salt.

Subsequently, a Pyrex beaker (volume, 200 ml) was charged with the recovered palladium on carbon and 100 ml of 0.365% HCl. The mixture was stirred for 30 minutes with a magnetic stirrer, adjusted to a pH of 11 with 25% aqueous sodium hydroxide and thereafter stirred for an additional 10 minutes. The palladium on carbon was filtered out through filter paper No. 5C, to obtain a regenerated palladium catalyst immersed in HCl.

Using the regenerated palladium on carbon, the second run of reaction was carried out under the same conditions as described above. The resulting reaction product was analyzed by liquid chromatography to determine the yield of S-BTC salt. The results of the first and second runs of reaction are shown in Table 5.

COMPARATIVE EXAMPLE 4

The procedures of Example 8 were repeated except that no catalyst immersion was conducted. The results are shown in Table 5.

TABLE 5

| Example No. | First Run Conversion (mol %) | First Run Yield of S-BTC salt (mol %) | Second Run Conversion (mol %) | Second Run Yield of S-BTC salt (mol %) |
|---|---|---|---|---|
| 8 | 100 | 55 | 100 | 53 |
| Comparative Example 4 | 100 | 54 | 100 | 47 |

COMPARATIVE EXAMPLE 5

Immersion of Pd Catalyst in H$_2$SO$_4$

A Pyrex beaker (volume, 100 ml) was charged with 2.35 wt % palladium on carbon containing 52.99% water (product of Japan Engelhardt Co., Ltd.) in an amount of 1.90 g (44.65 mg or 0.420 mmol as Pd) and 100 ml of 1.00% aqueous sulfuric acid. The mixture was stirred with a magnetic stirrer and filtered through filter paper No. 5C (Toyo Roshi Kaisha, Ltd.), to obtain a palladium catalyst on carbon that had been immersed in H$_2$SO$_4$.

Dimerization Reaction

A stainless steel separable flask (volume, 500 ml) was charged with all of the H$_2$SO$_4$ immersed palladium on carbon obtained above, 58.89 g of a white powder mainly comprised of monosodium 4-chlorophthalate (containing 145.4 mmol of monosodium 4-chlorophthalate, 20.0 mmol of monosodium 3-chlorophthalate, 9.3 mmol of monosodium 4,5-dichlorophthalate, 8.0 mmol of monosodium 3,4-dichlorophthalate, and 77.8 mmol of monosodium phthal-ate, 27.76 g (659.3 mmol) of 95 wt % sodium hydroxide, 137.4 ml of demineralized water and 13.1 g (211.1 mmol) of ethyl-ene glycol. After equipping the flask with a reflux condenser and a stirrer, the mixture was heated for 5 hours with stirring under atmospheric pressure at 107° C.

After the reaction, the reaction mixture was analyzed by liquid chromatography. The results are shown in Table 6.

COMPARATIVE EXAMPLE 6

The procedures of Comparative Example 5 were repeated except that the palladium on carbon was immersed in 1.00% aqueous nitric acid. The results are shown in Table 6.

COMPARATIVE EXAMPLE 7

The procedures of Comparative Example 5 were repeated except that no catalyst immersion was conducted. The results are shown in Table 6.

TABLE 6

| | | Catalyst Immersion | | | | |
|---|---|---|---|---|---|---|
| Comparative Example | Reducing Agent | Acid | Acid concentration (%) | Time (min) | Conversion (mol %) | Yield of S-BTC Salt (mol %) |
| 5 | ethylene glycol | H₂SO₄ | 1.0 | 30 | 89.6 | 45.3 |
| 6 | ethylene glycol | HNO₃ | 1.0 | 30 | 97.7 | 48.2 |
| 7 | ethylene glycol | — | — | — | 100 | 49.2 |

Note:
When the palladium catalyst was immersed in H₂SO₄ (Comparative Example 5) or in HNO₃ (Comparative Example 6), the yield of the end product was even lower than when the catalyst without being subjected to any treatment (Comparative Example 7), indicating that immersion in these acids was not effective at all.

While the invention has been described in detail and with reference to specific embodiments thereof, it will be apparent to one skilled in the art that various changes and modifications can be made therein without departing from the spirit and scope thereof.

What is claimed is:

1. A method of dehalogeno-dimerizing, in the presence of a palladium catalyst, water, a reducing agent, and a halogen acceptor, an aromatic halide compound selected from the group consisting of a halogenated phthalic acid, a salt thereof with an alkali metal, a halogenated phthalic acid anhydride, and mixtures thereof, which comprises immersing said palladium catalyst on a support in a hydrohalogenic acid prior to said dehalogeno-dimerizing.

2. A method according to claim 1 wherein the hydrohalogenic acid has a concentration of 0.01 to 1 wt %.

3. A method according to claim 1 wherein the hydrohalogenic acid is hydrochloric acid.

4. A method according to claim 1 wherein the immersion time ranges from 5 minutes to 3 hours.

5. A method according to claim 4 wherein the immersion time ranges from 10 minutes to 1.5 hours.

6. A method according to claim 1 wherein the temperature for the immersion treatment ranges from 5° to 70° C.

7. A method according to claim 1 wherein the aromatic halide compound is soluble in an aqueous alkaline solution.

8. A method according to claim 1 wherein the aromatic halide compound has 1 or 2 halogen atoms substituted on the aromatic ring, with 1 or 2 substituents other than halogen atoms being optionally substituted on the aromatic ring.

9. A method according to claim 1 wherein the aromatic halide compound is a benzene compound substituted by 1 or 2 halogen atoms and 1 or 2 carboxyl or hydroxyl groups.

10. The method of claim 1 wherein said aromatic halide compound is selected from the group consisting of a monohalogenophthalic acid, a salt thereof with an alkali metal, a monohalogenophthalic acid anhydride, and mixtures thereof.

11. A method according to claim 1 wherein the aromatic halide compound is at least one member selected from the group consisting of 4-chlorophthalic acid, a salt thereof with an alkali metal, and 4-chlorophthalic anhydride.

12. A method according to claim 1 wherein the reducing agent is at least one member selected from the group consisting of an alcohol, carbon monoxide, chloroform and a formaldehyde.

13. A method according to claim 12 wherein the reducing agent is an alcohol or carbon monoxide.

14. A method according to claim 13 wherein the reducing agent is an alcohol.

15. A method according to claim 14 wherein the reducing agent is a polyhydric alcohol.

16. A method according to claim 15 wherein the reducing agent is glycerin or ethylene glycol.

17. A method according to claim 1 wherein the reducing agent is used in an amount of 0.1 to 10 moles per mole of the aromatic halide compound.

18. A method according to claim 1 wherein the halogen acceptor is an alkali metal compound or an alkaline earth metal compound.

19. A method according to claim 1 wherein the halogen acceptor is a hydroxide of an alkali metal compound or an alkaline earth metal compound.

20. A method according to claim 1 wherein the halogen acceptor is used in an amount of 0.1 to 20 moles per mole of the aromatic halide compound.

21. A method according to claim 1 wherein the palladium catalyst on support has 0.5 to 10 wt % metallic palladium supported on an activated carbon carrier.

22. The method of claim 1 wherein said catalyst is present in an amount of 100 to 0.001 mg atoms per mol of said aromatic halide compound.

23. The method of to claim 22 wherein said amount is 30 to 0.01 mmol, calculated as Pd, per mol of said aromatic halide compound.

24. A method according to claim 1 wherein the reaction mixture obtained at the time when the dehalogenodimerization reaction has been substantially completed is subjected to an additional reduction in the presence of at least one post-reducing agent selected from the group consisting of hydrogen, formic acid, a salt thereof and a hydrazine.

25. A method according to claim 24 wherein the additional reduction is conducted at 50° to 200° C. for 0.5 to 3 hours.

* * * * *